(12) United States Patent
Ayinde et al.

(10) Patent No.: US 12,396,707 B2
(45) Date of Patent: Aug. 26, 2025

(54) SYSTEMS AND METHODS FOR AUTOMATED ULTRASOUND IMAGE RECORDING BASED ON QUALITY SCORES

(71) Applicant: EchoNous, Inc., Redmond, WA (US)

(72) Inventors: Babajide Ayinde, Redmond, WA (US); Timothy Crossley, Renton, WA (US); Matthew Cook, Woodinville, WA (US); Fan Zhang, Bellevue, WA (US)

(73) Assignee: EchoNous, Inc., Redmond, WA (US)

( * ) Notice: Subject to any disclaimer, the term of this patent is extended or adjusted under 35 U.S.C. 154(b) by 202 days.

(21) Appl. No.: 17/885,448

(22) Filed: Aug. 10, 2022

(65) Prior Publication Data

US 2024/0050069 A1    Feb. 15, 2024

(51) Int. Cl.
*A61B 8/00*    (2006.01)

(52) U.S. Cl.
CPC .............. *A61B 8/463* (2013.01); *A61B 8/54* (2013.01); *G06T 2207/10132* (2013.01)

(58) Field of Classification Search
CPC .. G06T 2207/10132; A61B 8/463; A61B 8/54
See application file for complete search history.

(56) References Cited

U.S. PATENT DOCUMENTS

| | | | |
|---|---|---|---|
| 8,922,633 B1 | 12/2014 | Pfeffer | |
| 2013/0190600 A1 | 7/2013 | Gupta et al. | |
| 2017/0273669 A1* | 9/2017 | Schneider | G06T 7/0012 |
| 2019/0130554 A1* | 5/2019 | Rothberg | G06T 7/0002 |
| 2020/0245976 A1* | 8/2020 | Cadieu | A61B 8/5207 |
| 2020/0261060 A1 | 8/2020 | Lundberg et al. | |
| 2021/0077068 A1 | 3/2021 | Lu et al. | |
| 2021/0298607 A1* | 9/2021 | Rani | A61B 5/7221 |
| 2021/0321979 A1 | 10/2021 | Sarnow et al. | |
| 2022/0338845 A1* | 10/2022 | Rafter | A61B 8/5223 |

(Continued)

FOREIGN PATENT DOCUMENTS

WO    2021/050976 A1    3/2021

OTHER PUBLICATIONS

International Search Report and Written Opinion of the International Searching Authority for Application No. PCT/US2023/029569, dated Nov. 22, 2023, 9 pages.

*Primary Examiner* — John D Li
(74) *Attorney, Agent, or Firm* — Seed Intellectual Property Law Group LLP

(57) ABSTRACT

Systems and methods for automated recording of an ultrasound clip are based on quality scores of ultrasound images in a sequence of ultrasound image frames. An ultrasound imaging system includes a probe for capturing ultrasound images, an image buffer to store a sequence of image frames, a quality buffer to store a sequence of quality scores, and a computing subsystem that automatically records an ultrasound clip when the quality scores in the quality buffer corresponding to a set of contiguous image frames in the image buffer equal or exceed a first quality threshold and the set of contiguous image frames is at least a first predetermined size. Additionally, a smart capture feature automatically records an ultrasound clip including an alternate set of contiguous image frames having quality scores equaling or exceeding a second quality threshold that is less than the first quality threshold and meets a second predetermined size.

22 Claims, 9 Drawing Sheets

(56) References Cited

U.S. PATENT DOCUMENTS

| | | | |
|---|---|---|---|
| 2022/0343495 A1* | 10/2022 | Urman | G06T 7/0012 |
| 2023/0148998 A1* | 5/2023 | Owen | A61B 8/5269 |
| | | | 600/437 |
| 2023/0401719 A1* | 12/2023 | Olivier | G06T 7/10 |

* cited by examiner

SYSTEMS AND METHODS FOR AUTOMATED ULTRASOUND IMAGE RECORDING BASED ON QUALITY SCORES

BACKGROUND

Technical Field

This disclosure generally relates to ultrasound imaging systems and methods and, more particularly, to systems and methods for automatically recording a clip of ultrasound images in a memory.

Description of the Related Art

Ultrasound imaging is typically performed in a clinical setting, by trained ultrasound experts. For diagnostic ultrasound imaging, particular views of an organ or other tissue or body feature (such as fluids, bones, joints or the like) are clinically significant. Such views may be prescribed by clinical standards as views that should be captured by an ultrasound technician, depending on the target organ, diagnostic purpose, or the like.

The image quality of acquired ultrasound images varies depending on a variety of factors, including, for example, the positioning of the probe, the imaging parameters (e.g., depth, gain, etc.), and so on. For clinical use (e.g., for diagnosis), ultrasound images generally should have suitable image quality. Clinicians generally require significant training in order to assess the diagnostic quality of ultrasound images. Such images can be obtained in real time during image acquisition or they can be previously acquired. In both cases, clinicians need to evaluate the level of diagnostic quality of the ultrasound images. Similarly, in training and educational settings, expert ultrasound users are required to grade the diagnostic quality of images acquired by students and novice users, and this is very time consuming for the ultrasound experts.

Moreover, significant training is generally required for clinicians to be able to recognize the anatomical structures present in an ultrasound image. This is particularly challenging during real time ultrasound image acquisition during which the ultrasound images continuously change as the position and orientation of the probe moves with respect to the organ or body feature of interest.

While conventional ultrasound imaging systems may be suitable for most patients in a hospital or similar clinical setting, such systems require significant training to operate and to adequately capture clinically desirable views. Such training requirements also extend to evaluation of ultrasound images in a sequence of image frames that comprise a video clip, to ensure that the images in the video clip adequately capture clinically desirable views. This adds to the overall cost of ultrasound imaging and further limits the availability of ultrasound imaging to patients, as only well-trained professionals can properly operate conventional ultrasound imaging devices.

BRIEF SUMMARY

In various embodiments, disclosed herein is an ultrasound imaging system that includes a probe with an ultrasound transducer and a computing subsystem with a processor, a non-volatile memory, and an image quality detector. The image quality detector may be implemented by the processor. Using the ultrasound transducer, which may be a transducer array, the probe transmits and receives ultrasound signals and thereby acquires ultrasound images arranged in a sequence of image frames. Each image frame contains an ultrasound image based on the ultrasound signals.

The ultrasound imaging system is configured to implement an automated capture feature that automatically identifies and saves a clip of ultrasound images in a sequence of image frames that feature a clinically-desirable view of an organ or other body feature as imaged by the ultrasound imaging system. In the present disclosure, references to "an organ" applies to an organ per se and also to other anatomical structures or body features of the patient. The image quality detector (e.g., an image evaluation process performed by a neural network in the computing subsystem) assigns a quality score, e.g., from 1-5, to each image frame of the sequence of image frames based on an evaluation of a quality of the ultrasound image in each image frame.

During ultrasound imaging, the ultrasound imaging system temporarily stores a sequence of image frames in an image buffer of a predetermined size (e.g., a cine memory for high-speed video recording). Depending on the size of the image buffer and the frame rate at which the ultrasound system acquires ultrasound images, the image buffer holds a sequence of image frames acquired over a period of time. Quality scores assigned to the ultrasound images in the sequence of image frames are stored in a quality buffer, in a sequence of quality scores that correspond respectively with the image frames in the sequence of image frames.

The image quality detector in the computing subsystem determines the quality score for the ultrasound image in each image frame and stores the quality score in the quality buffer. When the set of contiguous image frames reaches at least a first predetermined size and the quality score for each image frame in the set of contiguous image frames equals or exceeds a first quality threshold, the computing subsystem automatically records an ultrasound clip of the image frames from the image buffer to the non-volatile memory. In some examples, the computing subsystem may automatically record an ultrasound clip including only the set of contiguous image frames from the image buffer to the non-volatile memory where the quality score for each image frame in the set of contiguous image frames equals or exceeds a first quality threshold. In some cases, for example, the set of contiguous image frames may comprise 70% or more of the image frames in the image buffer, with each image frame having a quality score of at least 4 on a scale of 1-5. In this manner, the automated capture feature automatically retrospectively saves a clip of ultrasound image frames from the image buffer to the non-volatile memory.

In some embodiments, the computing subsystem is configured to provide a smart capture feature when a predetermined period of time has elapsed and the image buffer does not contain a set of contiguous image frames of at least the first predetermined size having corresponding quality scores equaling or exceeding the first quality threshold. Activation of the smart capture feature causes the computing subsystem to automatically record an alternate set of contiguous image frames from the image buffer when the quality score for each image frame in the alternate set of contiguous image frames equals or exceeds a second quality threshold, which may be lower than the first quality threshold. In various embodiments, the alternate set of contiguous image frames may have a predetermined size that is different than the first predetermined size of the set of contiguous image frames that otherwise would have been recorded by the automated capture feature if the quality scores of the image frames had met the first quality threshold. With these features, the systems and methods described herein provide for automatically recording a clip of ultrasound images that satisfy a desired image quality.

DETAILED DESCRIPTION

Embodiments of systems and methods described herein provide for automated recording of a clip of ultrasound images based on quality scores assigned to the ultrasound images. The systems and methods described herein may particularly be useful for ultrasound imaging performed by less experienced ultrasound technicians and/or for ultrasound imaging utilizing a handheld or mobile ultrasound imaging device that may be deployed in a non-traditional setting. Utilizing artificial intelligence approaches, embodiments of systems and methods described herein are capable of automatically assigning a quality score, e.g., from 1-5, to each acquired ultrasound image in a sequence of image frames based on an evaluation of a quality of the ultrasound image in each image frame.

The systems and methods described herein may include an image buffer, e.g., a cine memory of a predetermined size, to store a sequence of image frames. A quality score assigned to each image frame of the sequence of image frames may be stored in a separate quality buffer. In various embodiments, a computing subsystem may compare the quality scores in the quality buffer with a quality threshold. The computing subsystem may activate an automated capture feature to retrospectively store a clip of ultrasound image frames from the image buffer to a non-volatile memory when the quality scores for a set of contiguous image frames in the image buffer equal or exceed the quality threshold and the set of contiguous image frames is at least a predetermined size. Alternatively, the computing subsystem may activate a smart capture feature when, after a period of time, the image buffer does not contain a set of contiguous image frames whose ultrasound images have a quality score that equals or exceeds the quality threshold.

Figure 1:
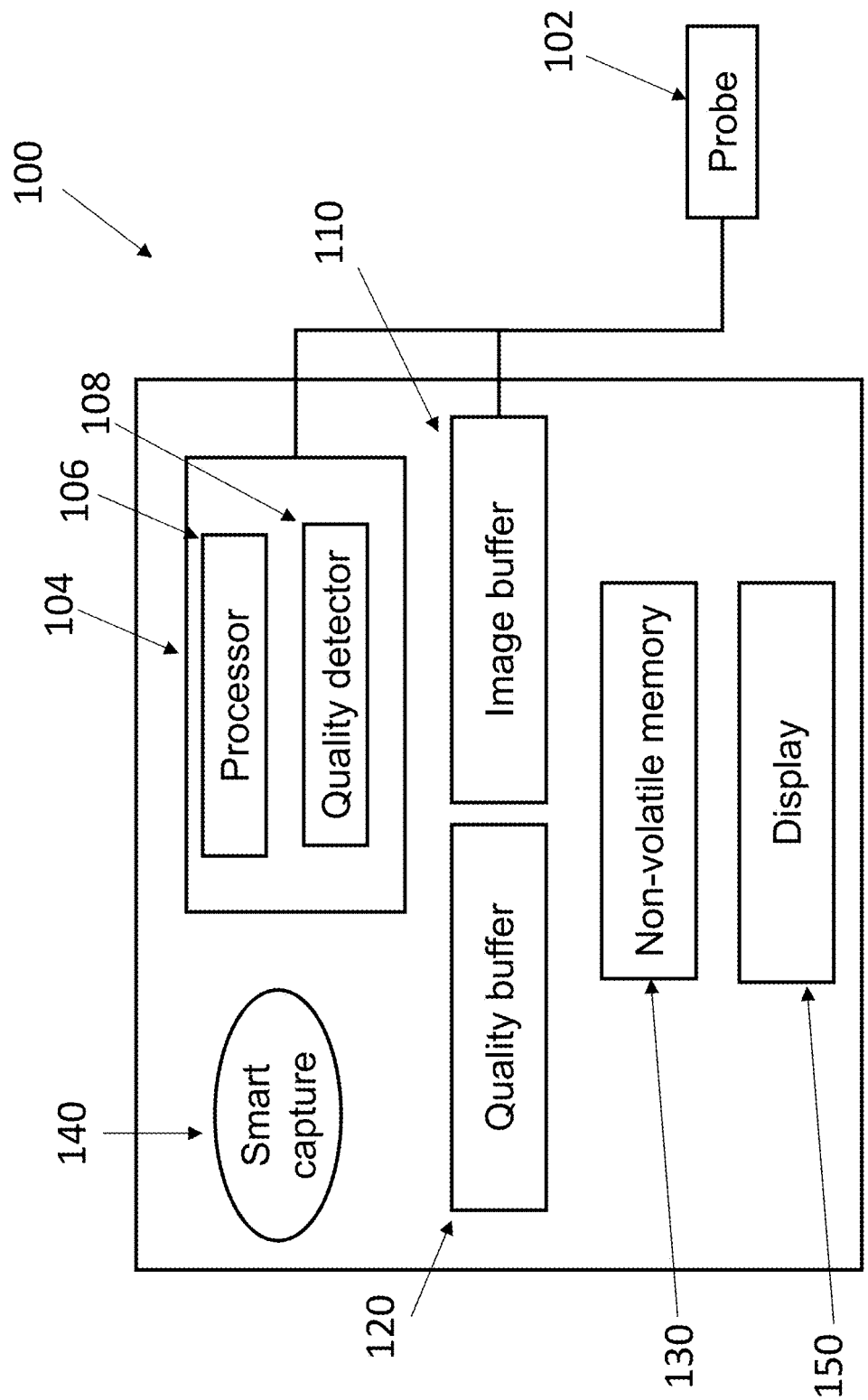
FIG. 1 is a block diagram illustrating an ultrasound imaging system for automated ultrasound image recording based on quality scores, in accordance with one or more embodiments of the disclosure.

FIG. 1 is a block diagram of one example of an ultrasound imaging system 100 configured to automatically record ultrasound images as a clip based on quality scores of the ultrasound images. The ultrasound imaging system 100 is comprised of an ultrasound imaging device that includes a computing subsystem 104, an image buffer 110, a quality buffer 120, a non-volatile memory 130, and optionally a smart capture button 140 and a display 150. Each of these may be incorporated into a single ultrasound imaging device, such as a hand-held or portable device, or may constitute multiple devices operatively linked or linkable to one another by communication or by electrical connection. As will be described in further detail herein, the computing subsystem 104 may include a processor 106 and at least one image quality detector 108, each of which may include programmed and/or hardwired circuitry configured to perform the functions or actions described herein.

The ultrasound imaging system 100 is operable to acquire ultrasound images of a patient, and may be, in at least some embodiments for example, a handheld ultrasound imaging device. The ultrasound imaging system 100 is operatively coupled to an ultrasound probe 102, or may be incorporated into the ultrasound probe 102.

The non-volatile memory 130 may be a non-volatile storage medium such as, for example, flash memory, hard disk drive, optical storage device, magnetic storage device, organic storage media, or the like, and may be configured for fast storage of image frames.

The processor 106 may be any computer processor operable to execute instructions (possibly stored in memory 130) that cause the processor 106 perform the functions of the ultrasound imaging system 100 as described herein.

The ultrasound probe 102 includes one or more ultrasound transducers that are driven by the ultrasound imaging system 100 to transmit ultrasound signals toward a target region in a patient, and to receive echo signals returning from the target region in response to the transmitted ultrasound signals. In operation, a user of the ultrasound imaging system 100 may hold the probe 102 against a patient's body at a position and angle to acquire desired ultrasound images. The signals received by the probe (i.e., the echo signals) are converted to electronic signals that are communicated to the ultrasound imaging device 100 and may form, or be processed to form, ultrasound images of the target region in the patient. The ultrasound images are stored in the image buffer 110. In some examples, the ultrasound imaging system 100 may include a display 150 that can display the ultrasound images and/or other relevant information to the user.

In some embodiments, the image quality detector 108 receives the ultrasound images acquired by the ultrasound probe 102, automatically determines an image quality for each of the received ultrasound images, and automatically assigns a quality score to each of the ultrasound images based on the determined image quality. For example, in some embodiments, the quality score may be a value between 1 and 5. In this fashion, a quality score of 1 may represent a lowest image quality while a quality score of 5 may represent a highest image quality.

In some examples, the image quality detector 108 includes machine learning circuitry (implemented by software, hardware, or a combination thereof) that receives the ultrasound images acquired by the ultrasound imaging system 100, and automatically determines an image quality score for each of the received ultrasound images. In some embodiments, an ultrasound image grading module (which may be included as part of the machine learning circuitry) automatically determines the image quality scores and stores the quality scores in the quality buffer 120.

In some embodiments, an ultrasound image recognition module (which may be included as part of the machine learning circuitry) may be used to automatically determine whether one or more of the acquired ultrasound images represents a clinically desirable view of an organ or other aspect, region, or feature of the patient. In some cases, the machine learning circuitry may also be configured to automatically label one or more anatomical structures in the ultrasound images. For example, an anatomical structure recognition and labeling module (which may be included as part of the machine learning circuitry) may automatically recognize anatomical structures in the ultrasound images, and automatically associate labels with the recognized anatomical structures. In some embodiments, the labels associated with the recognized anatomical structures are displayed (e.g., on the display 150) superimposed on or embedded within the ultrasound image in a region where the corresponding anatomical structures are displayed.

Each of the ultrasound image recognition module, the anatomical structure recognition and labeling module, and the ultrasound image grading module may be implemented by a computationally intelligent system that employs artificial intelligence, drawing from an image knowledge database, to perform the functions of these modules as described herein (e.g., determining whether received ultrasound images represent a clinically desirable view, recognizing and labeling anatomical structures in the ultrasound images, and determining an image quality score for each of the ultrasound images in a sequence of image frames). Suitable processes for training the machine learning circuitry and generating the image knowledge database that is used by the ultrasound image recognition module, the structure recognition and labeling module, and the ultrasound image grading module are described, for example, in U.S. Pre-Grant Publication No. 2021/0077068 A1, which is assigned to the assignee of the present disclosure and expressly incorporated by reference herein.

As noted, in at least some embodiments, the image quality detector 108 uses a computationally intelligent system that employs artificial intelligence to determine the quality score for each of the acquired ultrasound images. "Artificial intelligence" is used herein to broadly describe computationally intelligent systems and methods that can learn knowledge (e.g., based on training data) and use such learned knowledge to adapt its approaches for solving one or more problems. Artificially intelligent machines may employ, for example, neural network, deep learning, convolutional neural network, and Bayesian program learning techniques to solve problems such as image recognition, anatomical structure recognition and labeling, and image quality grading. Further, artificial intelligence may include any one or combination of the following computational techniques: constraint program, fuzzy logic, classification, conventional artificial intelligence, symbolic manipulation, fuzzy set theory, evolutionary computation, cybernetics, data mining, approximate reasoning, derivative-free optimization, decision trees, and/or soft computing.

In various embodiments, the machine learning circuitry may be trained based on training images. Training images may include any ultrasound image information. For example, the training images may include image information used to train the ultrasound image grading module, e.g., used by the image quality detector 108. The training images may include a variety of ultrasound images of different image qualities (e.g., higher quality images, lower quality images, blurry images, and so on). The qualities of the training images used to train the ultrasound image grading module may first be graded by an expert such as a physician or other clinician. The qualities of the training images may be graded based on any grading system. In some embodiments, the qualities of the training images may be graded based on a standard grading system, such as the American College of Emergency Physicians (ACEP) grading rubric provided in Table 1 below.

TABLE 1

| | [ACEP Image Quality Grading Rubric] | | | | |
| --- | --- | --- | --- | --- | --- |
| | Scoring Criteria | | | | |
| | 1 | 2 | 3 | 4 | 5 |
| ACEP Image Quality Grading Rubric | No recognizable structures, no objective data can be gathered | Minimally recognizable structures but insufficient for diagnosis | Minimal criteria met for diagnosis, recognizable structures but with some technical or other flaws | Minimal criteria met for diagnosis, all structures imaged well and diagnosis easily supported | Minimal criteria met for diagnosis, all structures imaged with excellent image quality and diagnosis completely supported |

Each of the training images may be assigned a particular quality score or grade (e.g., 1 through 5) by a physician or other clinician, with the assigned quality score or grade representing a quality of the training image.

In embodiments with an ultrasound image recognition module, the training images may include image information used to train the ultrasound image recognition module, such as a variety of ultrasound image information associated with known views of an organ, such as the heart. As a further example, the training images may be clinically desirable images of, e.g., suprasternal views of a heart. In such a case, the training images may be ultrasound images that have been pre-determined (e.g., by a physician or other trained expert) as adequately showing a clinically desirable suprasternal view of the heart. Each such training image may have slightly different characteristics (e.g., higher quality images, lower quality images, blurry images, images taken at slightly different angles, and so on), yet each such training image may nonetheless be pre-determined as adequately representing a clinically desirable view of the heart or other anatomical structure or body feature.

Moreover, the training images may include not only image information associated with clinically standard or desirable views, but may further include image information associated with non-clinically standard or non-clinically desirable views. Accordingly, the ultrasound image recognition module may receive, for example, a view of a heart that does not represent a particular clinically desirable view (e.g., a suprasternal, subcostal, short- and long-axis parasternal, 2-chamber apical, 3-chamber apical, 4-chamber apical and 5-chamber apical view). In such a case, the ultrasound recognition module may nonetheless be trained to recognize the image as being a view of a heart, and may further recognize the image as being an image somewhere between, for example, a 2-chamber apical view and a 3-chamber apical view. A clinically standard 3-chamber apical view is generally obtainable, for example, by rotating an ultrasound imaging probe about 60° counterclockwise with respect to the 2-chamber apical view. Ultrasound images obtained with the probe at an angle of rotation somewhere between, for example, 5° and 55° counterclockwise with respect to the 2-chamber apical view may be determined as not representing a clinically desirable view of the heart.

Additionally, the ultrasound image recognition module may be trained with training images showing a variety of known, but non-clinically desirable, views of a heart (such as views somewhere between the 2-chamber apical and the 3-chamber apical views), and thus may recognize such views (e.g., the ultrasound image recognition module may recognize a view as representing a 35° counterclockwise rotation of the probe 102 with respect to the 2-chamber apical view). In some embodiments, upon recognizing an ultrasound image as containing a known non-clinically desirable view, guidance may be provided to the user to move the ultrasound probe in a specified manner that ultimately achieves acquisition of a clinically desirable view.

In some embodiments, the training images may include image information used to train an anatomical structure recognition and labeling module. For example, the training images may include a variety of ultrasound image information associated with known anatomical structures, such as particular organs (e.g., the heart) or particular features of organs (e.g., left ventricle, right ventricle, left atrium, right atrium, mitral valve, tricuspid valve, aortic valve, etc.). Further, the training images may include image information associated with such known anatomical structures from a variety of different views. Anatomical structures may appear very different across different views, e.g., the left ventricle may appear different in ultrasound images acquired at various different views (e.g., apical-LV, parasternal long-LV, parasternal long-LV). Therefore, ultrasound images representing known anatomical structures (e.g., the left ventricle) in a variety of different views may be provided as training images, which may be utilized to train the anatomical structure recognition and labeling module to recognize not only the anatomical structure but also the particular view provided by the ultrasound image.

Other training input may further be provided to the ultrasound image recognition module for training. The other training input may include, for example, manually-entered input to adjust or otherwise manage the image recognition model developed in the image recognition module through the training process.

Using training images, the machine learning circuitry (including the ultrasound image grading module, the ultrasound image recognition module, and/or the anatomical structure recognition and labeling module) may implement an iterative training process. Training may be based on a wide variety of learning rules or training algorithms. For example, the learning rules may include one or more of the following: back-propagation, real-time recurrent learning, pattern-by-pattern learning, supervised learning, interpolation, weighted sum, reinforced learning, temporal difference learning, unsupervised learning, and/or recording learning.

Returning now to FIG. 1, in various embodiments the image buffer 110 may be a temporary storage (e.g., volatile memory) with a predetermined size. In some examples, the image buffer 110 may store a sequence of image frames acquired by the probe 102. In some embodiments, the size of the image buffer 110 may be configured to be the same as or greater than a length of an ultrasound clip to be recorded. For instance, the length of an ultrasound clip may be configured as 3 seconds, 5 seconds, 10 seconds, or 20 seconds. In such cases, the image buffer 110 is sized to be able to store a sequence of image frames that provides an ultrasound clip that is 3 seconds, 5 seconds, 10 seconds, or 20 seconds in length. In some examples, the image buffer 110 may be a circular or ring buffer, and storing image frames in the image buffer 110 may include deleting an oldest image frame from the image buffer 110 and adding a new image frame to the image buffer 110, on a rolling basis. In such examples, the quality buffer 120 may also be a circular or ring buffer, and the quality score for the oldest image frame would be deleted from the quality buffer 120 while the quality score for the new image frame being added would be added to the quality buffer 120, on a rolling basis.

In various embodiments, the quality score for each image frame stored in the image buffer 110 is stored separately in the quality buffer 120. In some examples, the quality buffer 120 may be a temporary storage (e.g., volatile memory) having a number of logical storage locations that equals the number of logical storage locations in the image buffer 110 for storing ultrasound image frames. In this fashion, the image quality detector 108 can be configured to assign a quality score to the ultrasound image in each acquired image frame and store the assigned quality score in the quality buffer 120 such that the quality scores in the quality buffer 120 correspond with respective image frames in the image buffer 110. In various embodiments, the quality buffer 120 may be implemented in a memory device different than the image buffer 110 or in the same memory device as the image buffer 110.

According to an automated capture feature described herein, the processor 106 may evaluate the quality score assigned to each of the acquired image frames by comparing the quality score with a first quality threshold. In some examples where the quality scores are values between 1 and 5, the first quality threshold used by the automated capture feature may be a score of 4 on the scale of 1 to 5. In some examples, the processor 106 may begin comparing the quality scores of the image frames stored in the image buffer 110 with the first quality threshold when (in response to or after) a predetermined amount of quality scores are stored in the quality buffer 120 or a predetermined period of time has elapsed in which quality scores have been stored in the quality buffer 120.

If the processor 106 determines that each of the image frames in a set of contiguous image frames in the image buffer 110 has a corresponding quality score that is equal to or greater than the first quality threshold, and the set of contiguous image frames has reached at least a first predetermined size, the processor 106 activates the automated capture feature described herein in which an ultrasound clip comprised of the set of contiguous image frames in the image buffer 110 is automatically recorded, e.g., in the non-volatile memory 130. In some examples, the processor 106 may continue acquiring images for the current region of interest, direct the image acquisition to a new region of interest, or cease image acquisition. The automated capture feature may cause the processor 106 to retrospectively record an ultrasound clip to the non-volatile memory 130 that includes all of the image frames stored in the image buffer 110, or in some cases, an ultrasound clip that includes less than all of the image frames in the image buffer 110, encompassing a shorter period of time than the time period otherwise encompassed by all of the image frames stored in the image buffer 110.

In some embodiments, the processor 106 may continue to automatically record, e.g., in the non-volatile memory 130, additional image frames from the image buffer 110 that are contiguous with the set of contiguous image frames that has already been recorded or identified to be recorded, wherein the additional image frames have quality scores that equal or exceed the first quality threshold. In yet other embodiments, the processor 106 may be configured to automatically record additional image frames from the image buffer 110 that are contiguous with the already-recorded set of contiguous image frames but have one or more quality scores that do not equal or exceed the first quality threshold. Thus, the processor 106 may stop recording image frames from the image buffer 110 to the non-volatile memory 130 when the ultrasound clip comprised of the set of contiguous image frames is recorded, and in some cases later when a quality score of a newly acquired image frame is less than the first quality threshold or when a maximum number of contiguous image frames is recorded.

In some embodiments, the processor 106 may be configured to provide a smart capture feature when, after a predetermined period of time has elapsed in which ultrasound images have been acquired, the processor 106 determines that the image buffer 110 does not contain a set of contiguous image frames of at least the first predetermined size having corresponding quality scores equaling or exceeding the first quality threshold. In such embodiments, the smart capture feature may be provided and activated. Activation of the smart capture feature causes the processor 106 to automatically record an ultrasound clip that includes an alternate set of contiguous image frames from the image buffer 110 when the quality score for each image frame in the alternate set of contiguous image frames equals or exceeds a second quality threshold. Typically, the second quality threshold is less than the first quality threshold. Thus, according to an automated capture feature, the ultrasound imaging system 100 initially attempts to automatically record an ultrasound clip of higher quality images, but if the quality scores of the acquired ultrasound images fail to reach the higher, first quality threshold, for a set of contiguous image frames of at least a first predetermined size, the ultrasound imaging system 100 provides an smart capture option to record an ultrasound clip comprised of an alternate set of contiguous image frames of at least a second predetermined size (e.g., as a "best available quality" clip) where the ultrasound images in the alternate set meet a lesser, second quality threshold. The second predetermined size of the alternate set of contiguous image frames may be smaller than, or in some cases equal to or larger than, the first predetermined size of the (initial) set of contiguous image frames.

In some examples, the smart capture feature provides a user-selectable smart capture button 140 that, when selected by a user of the ultrasound imaging system 100, activates the smart capture feature that enables the processor 106 to automatically record the alternate set of contiguous image frames from the image buffer 110. In this fashion, the user may choose whether to select the smart capture button 140 and automatically record an ultrasound clip comprised of an alternative contiguous portion of the sequence of image frames in the image buffer 110, e.g., as a "best available" image quality clip. In some embodiments, the smart capture feature may automatically be activated and automatically record the ultrasound clip comprised of the alternate set of contiguous image frames in the non-volatile memory 130, without waiting for a user input.

Figure 2:
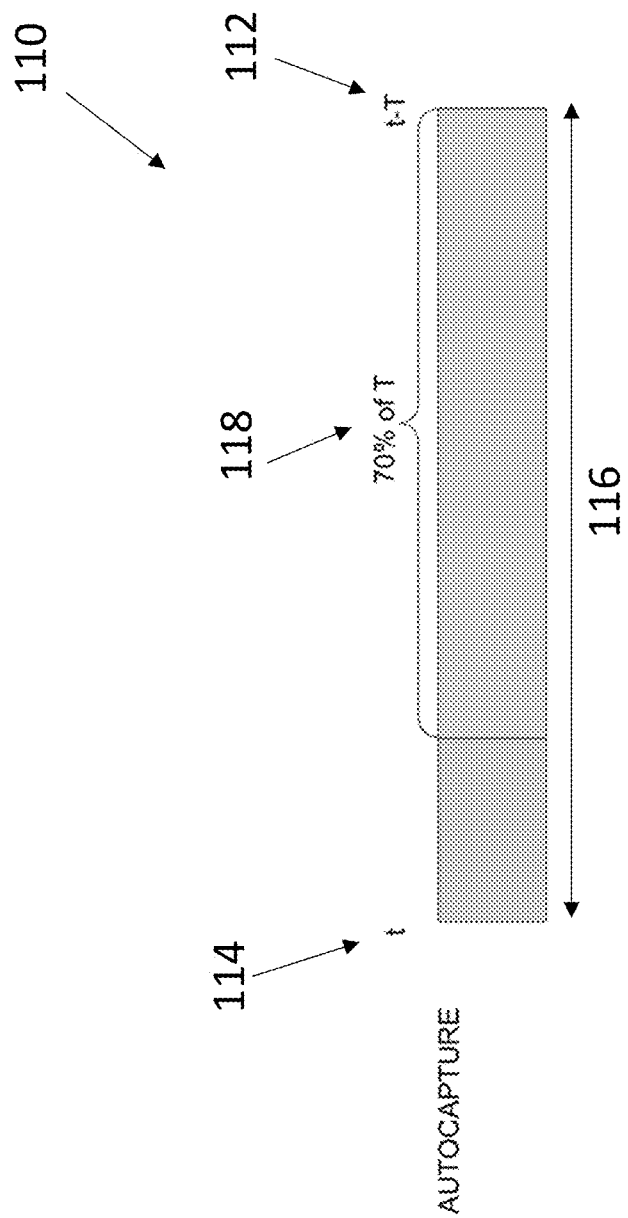
FIG. 2 is a schematic illustration of storing a sequence of image frames in an image buffer of a predetermined size, and identifying a set of contiguous image frames in the image buffer having quality scores that equal or exceed a first quality threshold, in accordance with one or more embodiments of the disclosure.

FIG. 2 is a schematic illustration of one example of an image buffer 110 in a condition to be processed by the automated capture feature described above. In this embodiment, the image buffer 110 has a predetermined size 116. A sequence of image frames is stored in the image buffer 110 starting at a time "t-T" 112 through a time "t" 114. A temporal length of the stored sequence of image frames is equal to time T, which is the difference between the times 112 and 114.

As described earlier with regard to FIG. 1, the processor 106 may be configured to automatically record an ultrasound clip including a set of contiguous image frames from the image buffer 110 when the quality score for each image frame in the set of contiguous image frames equals or exceeds a first quality threshold, and the set of contiguous image frames has at least a first predetermined size. The first predetermined size of the set of contiguous image frames may be a first predetermined portion of the image buffer 110. By way of example, the set of contiguous image frames may have a first predetermined size that is a defined percentage of the size 116 of the image buffer 110.

In FIG. 2, a contiguous set of image frames 118 comprises 70% of the size 116 of the image buffer 110. Accordingly, the set of contiguous of image frames 118 represents a clip of ultrasound images encompassing at least 70% of the time period covered by the image frames that are stored in the image buffer 110. In some other examples, the set of contiguous image frames 118 may have a first predetermined size that is more or less than 70% of the size 116 of the image buffer 110.

By way of example, in embodiments of the present disclosure where the quality of ultrasound images is measured on a scale of 1 to 5, the first quality threshold may be set at a quality score of 4. However, the processor 106 may operate using different scales and different quality thresholds depending on the quality standards implemented by the ultrasound imaging system 100.

When evaluating the quality scores in the quality buffer 120, the processor 106 may identify when the quality scores of a contiguous portion of the sequence of image frames in the image buffer 110 is equal to or greater than the first quality threshold (e.g., 4) and the size of the contiguous portion of the sequence of image is at least a first predetermined size. When such conditions are met, the automated capture feature causes the processor 106 to automatically retrospectively record an ultrasound clip, e.g., from the image buffer 110 to the non-volatile memory 130. The length of time of the ultrasound clip may be specified by the ultrasound imaging system 100 or set by a user of the ultrasound imaging system 100. Depending on the frame rate of the ultrasound imaging device that acquired the ultrasound image frames, the number of image frames in the ultrasound clip may vary. Thus, to automatically record an ultrasound clip of a desired length of time, as described herein, the ultrasound imaging system 100 may be configured to record an ultrasound clip comprised of a set of contiguous image frames that includes at least a predetermined number of image frames.

Figure 3:
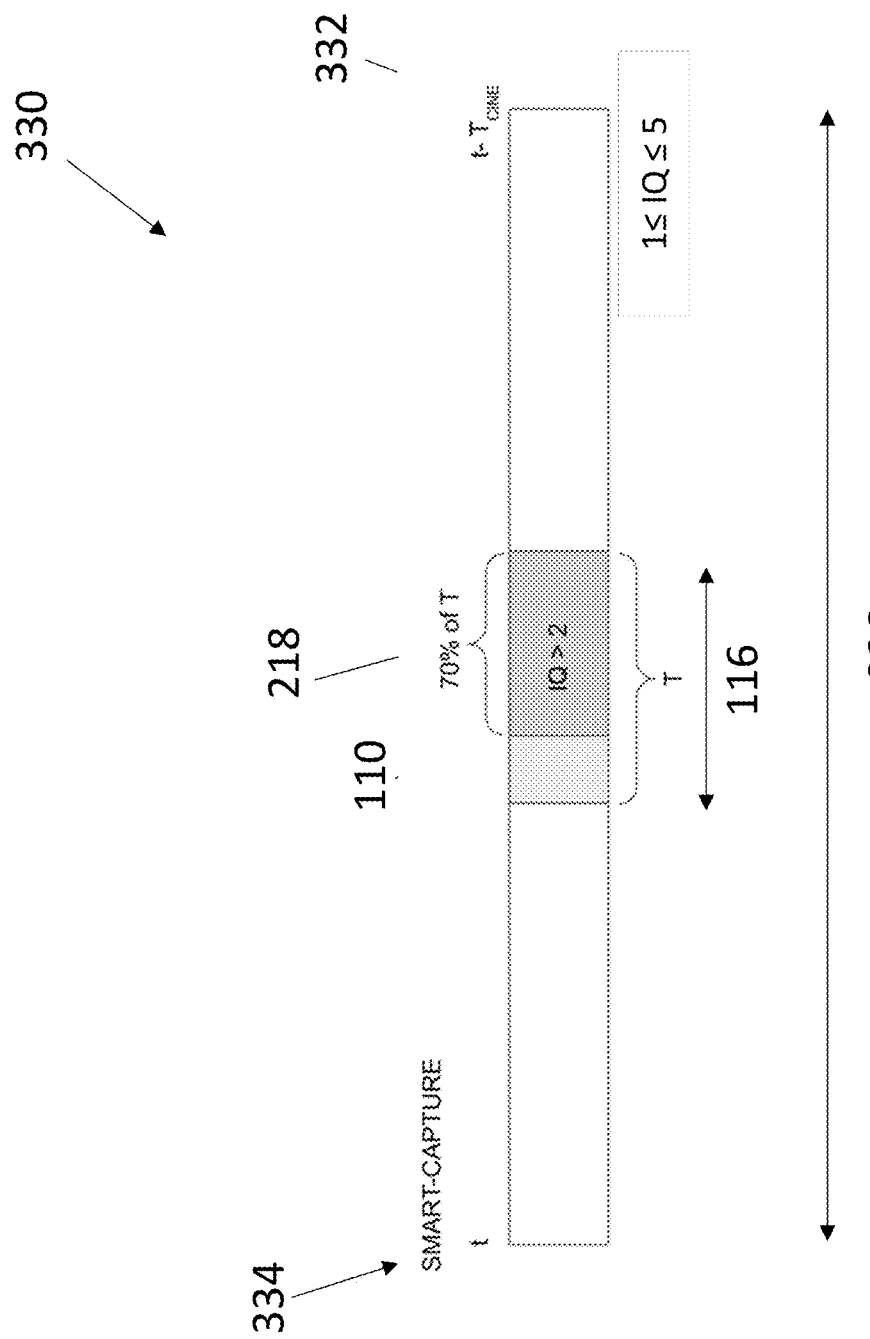
FIG. 3 is a schematic illustration of identifying an alternate set of contiguous image frames in an image buffer having quality scores that equal or exceed a second quality threshold, and recording the alternate set of contiguous image frames in a non-volatile memory, in accordance with one or more embodiments of the disclosure.

FIG. 3 is schematic illustration of an example in which the quality of the image frames in the image buffer 110 are not in a condition for automatically recording an ultrasound clip according to the automated capture feature described above with respect to FIG. 2. In the example of FIG. 3 however, a smart capture feature may be activated that causes the ultrasound imaging system 100 to record an ultrasound clip comprised of an alternate set of contiguous image frames, e.g., as described earlier herein.

FIG. 3 depicts a high speed buffer (e.g., cine) memory 330 that may have a predetermined size 336 and store one or more sequences of image frames ranging from a time "t-$T_{CINE}$" 332 to a time "t" 334. In FIG. 3, the image buffer 110 is illustrated as being a portion of the buffer memory 330, wherein the image buffer 110 is smaller in size than the buffer memory 330.

In the example shown in FIG. 3, the image buffer 110 does not have a set of contiguous image frames with corresponding quality scores equaling or exceeding the first quality threshold, as described with respect to FIG. 2. In this case, the processor 106 may be configured to provide a smart capture button 140 that enables a recording of an alternate ultrasound clip (e.g., a recording of an alternate set of contiguous image frames from the image buffer 110 having a "best available" quality).

A user of the ultrasound imaging system 100 may select the smart capture button 140 and cause the system 100 to record an alternate ultrasound clip of a predetermined size (e.g., time period T) when the alternate set of contiguous image frames 218 has quality scores that equal or exceed a second quality threshold and the alternate set of contiguous image frames 218 has at least a second predetermined size. The second quality threshold is generally lower than the first quality threshold. By way of non-limiting example, the second predetermined size may be about 70% of the predetermined size 116 (or time period T) of the image buffer 110. In some examples, the predetermined size 116 (or time period T) may be about 3 seconds, and the alternate set of contiguous image frames 218 may be least 2 seconds in length and have quality scores that meet or exceed the second quality threshold in order to be automatically recorded in the non-volatile memory 130. In some examples, the second quality threshold may be a quality score of 3 on a scale of 1 to 5, or a quality score of 2 on a scale of 1 to 5. In various embodiments, the size and quality criteria (i.e., the length of the set of contiguous image frames and the quality thresholds described herein) are adjustable according to the needs or specifications of the ultrasound imaging system 100.

In some embodiments, when a user selects the smart capture button 140, the processor 106 determines if the image buffer 110 contains an alternate set of contiguous image frames 218 of at least the second predetermined size that meets the quality criteria specified for the smart capture feature. If the size and quality criteria are met, the processor 106 records an ultrasound clip of the image frames from the image buffer 110 to the non-volatile memory 130. However, if the processor 106 fails to identify an alternate set of contiguous image frames 218 that meets the size and quality criteria, the processor 106 may send an error message to the display 150 to notify the user that a clip was not recorded in the non-volatile memory 130, at which point the user may wish to try again to acquire higher quality ultrasound images. In some examples, the processor 106 may automatically provide the smart capture feature or remove the smart capture feature without a user's input. The smart capture button 140 may be removed by the processor 106 when quality scores of the image frames in the image buffer 110 meet the first quality threshold used by the (initial) automated capture feature.

Figure 4:
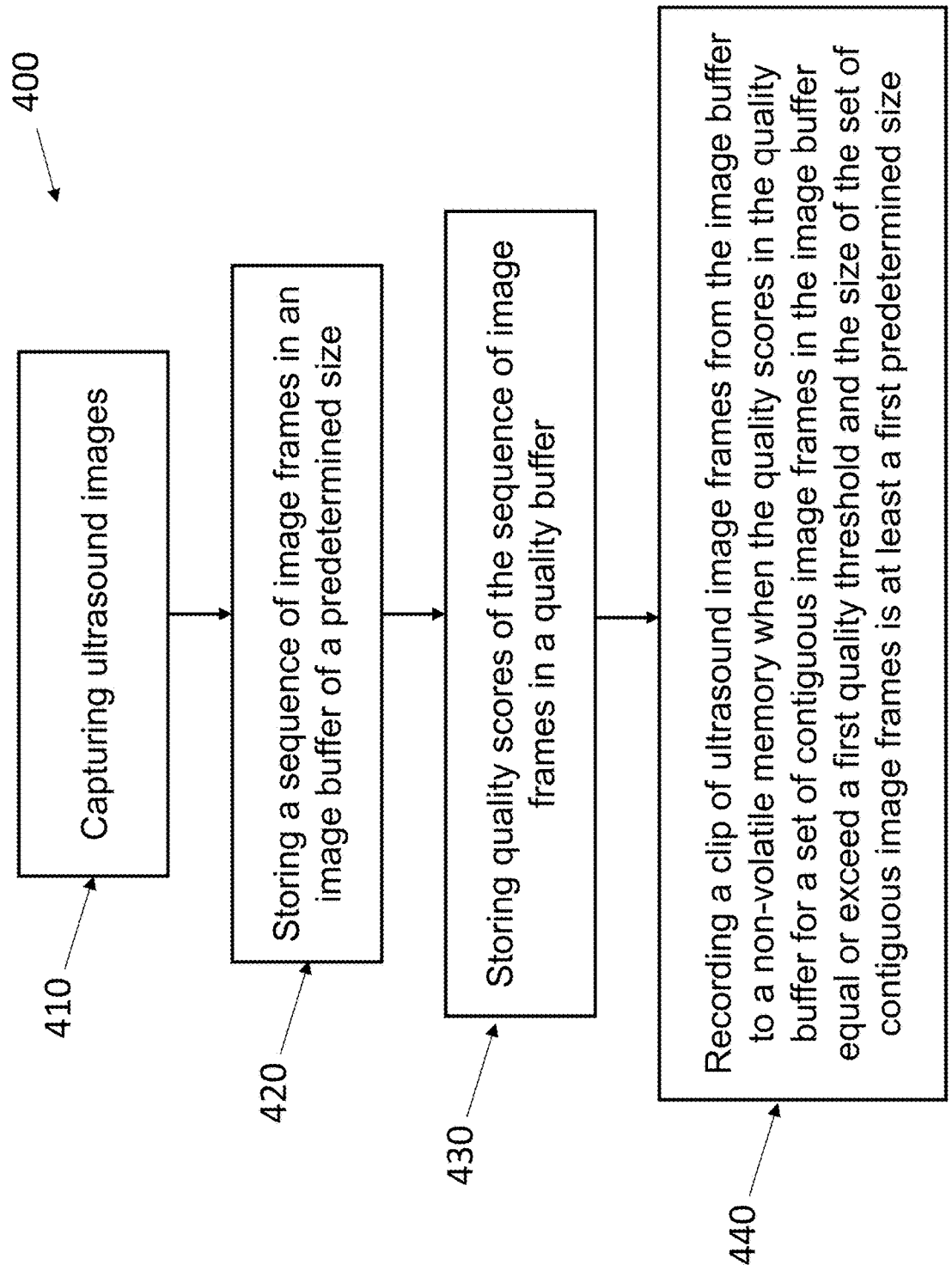
FIG. 4 is a flowchart illustrating an automated process for recording an ultrasound image clip based on quality scores of image frames in a set of contiguous image frames, in accordance with one or more embodiments of the disclosure.

FIG. 4 is a flowchart 400 illustrating a process for an automated ultrasound image clip recording based on the quality scores of a sequence of ultrasound image frames, e.g., as described in FIGS. 1 and 2. At step 410, ultrasound images are captured by an ultrasound probe such as the probe 102 described in FIG. 1. In operation, a user of the ultrasound imaging system 100 may hold the probe 102 against a patient's body at a position and angle to acquire desired ultrasound images. The signals received by the probe 102 (i.e., the echo signals) are communicated to the ultrasound imaging system 100 and may form, or be processed to form, a sequence of ultrasound images of a target region of the patient. Further, the ultrasound images may be provided to the display 150, which may display the ultrasound images and/or any other relevant information to the user.

At step 420, a sequence of image frames containing the ultrasound images is stored in an image buffer such as the image buffer 110 described in FIGS. 1-3. In some examples, as described above, storing image frames in the image buffer 110 may include deleting an oldest image frame from the image buffer 110 and adding a new image frame to the sequence of image frames stored in the image buffer 110.

At step 430, a quality score for each image frame of the sequence of image frames is determined by an image quality detector (e.g., image quality detector 108) and stored in a quality buffer (e.g., quality buffer 120) described in FIG. 1. In some cases, steps 420 and 430 may performed concurrently, i.e., quality scores are determined and stored concurrently with capturing the respective ultrasound images. At step 440, a processor implementing the automated capture feature may evaluate the quality scores in the quality buffer to determine if the quality scores of a contiguous portion of the image frames in the image buffer equal or exceed a first quality threshold and the contiguous portion of the image frames is at least a first predetermined size. If so, the automated capture feature causes the processor 106 to retrospectively record a clip of the ultrasound image frames from the image buffer to the non-volatile memory. The recorded clip includes at least the contiguous portion of the image frames in the image buffer that meet the quality and size criteria.

Figure 5:
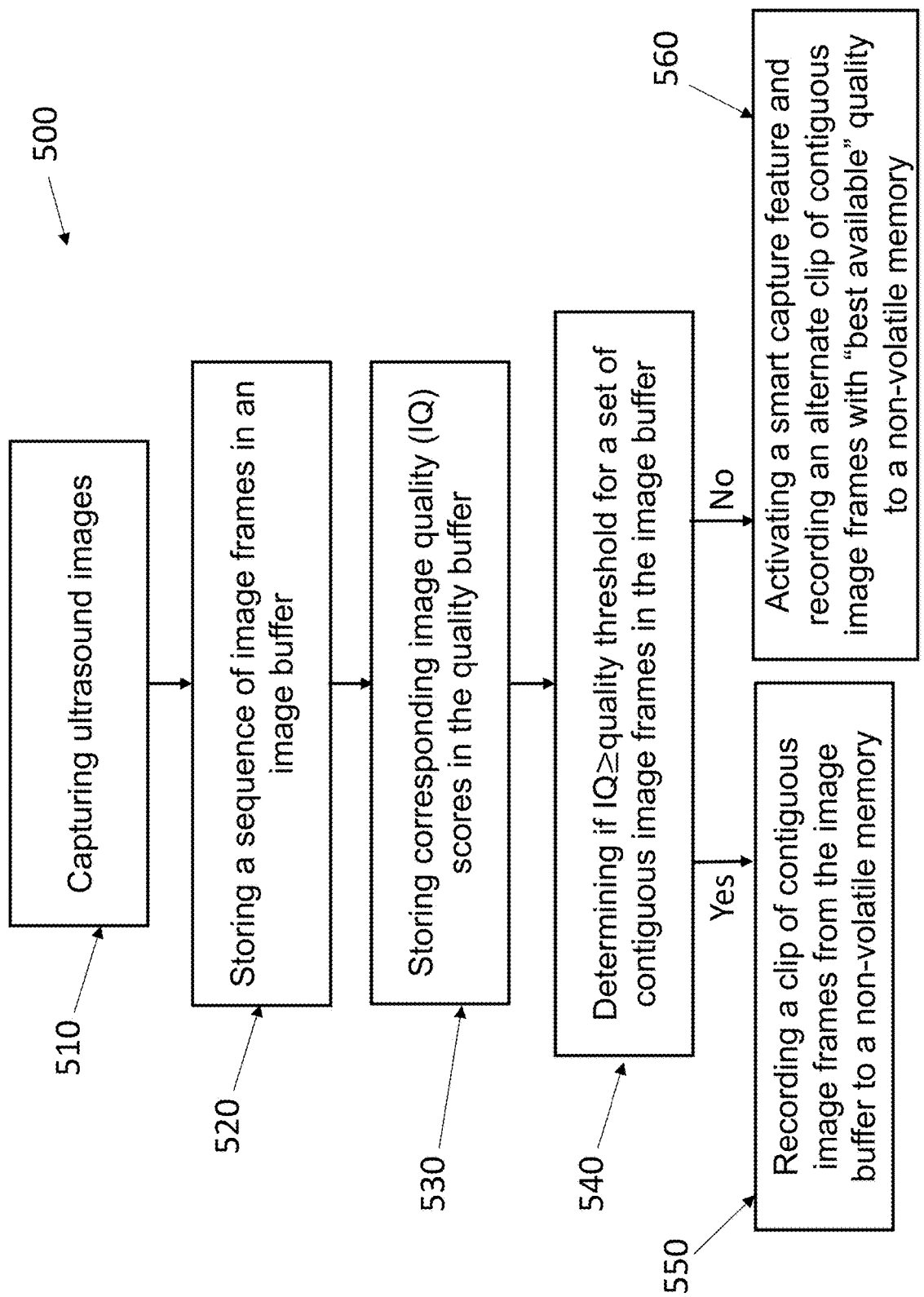
FIG. 5 is a flowchart illustrating a process for activating a smart capture feature that can automatically record an alternate set of contiguous image frames based on quality scores that equal or exceed a second quality threshold, in accordance with one or more embodiments of the disclosure.

FIG. 5 is a flowchart 500 illustrating a process that includes recording an ultrasound clip using an automated capture feature or, alternatively, a smart capture feature, based on the quality scores of image frames stored in the image buffer, e.g., as described in FIGS. 1-3. At step 510, ultrasound images are captured by a probe such as the probe 102 described in FIG. 1. At 520, the ultrasound images are stored in a sequence of image frames in an image buffer such as the image buffer 110 described in FIGS. 1-3.

At 530, a quality score for each of the image frames stored in an image buffer is determined by an image quality detector and stored in a quality buffer (e.g., the quality buffer 120 described in FIG. 1). At 540, a processor of the ultrasound imaging system 100 evaluates the quality scores in the quality buffer and determines whether a set of contiguous image frames in the image buffer have quality scores that equal or exceed a quality threshold, such as the first quality threshold described herein. If the quality scores in the quality buffer indicate that the image buffer contains a set of contiguous image frames of a first predetermined size having quality scores that equal or exceed the first quality threshold, the processor proceeds to step 550 where the processor automatically records a clip comprised of at least the set of contiguous ultrasound image frames from the image buffer to the non-volatile memory. On the other hand, if at step 540, after a period of time has elapsed and the processor determines that the image buffer does not contain a set of contiguous image frames of at least the first predetermined size having quality scores that equal or exceed the first quality threshold, the processor proceeds to step 560 and provides a smart capture feature, e.g., a smart capture button 140 as described with respect to FIGS. 1 and 3. A user of the ultrasound imaging system 100 may select the smart capture button 140 which enables the system 100 to automatically record an alternate set of contiguous image frames of a second predetermined size having quality scores that equal or exceed a second quality threshold. The second quality threshold may be a lower quality threshold than the first quality threshold.

The alternate set of contiguous image frames may constitute an ultrasound clip that includes contiguous image frames from the image buffer having a "best available" quality. As described in FIG. 3, the alternate set of contiguous image frames may be stored in the non-volatile memory 130. If the ultrasound imaging system 100 cannot identify an alternate set of contiguous image frames that meets the second predetermined size and quality criteria, the processor of the ultrasound imaging system 100 may send an error message to a display to indicate that a clip was not recorded in the non-volatile memory, at which point the ultrasound imaging system 100 may return to step 510, allowing the user to capture higher quality images.

Figure 6:
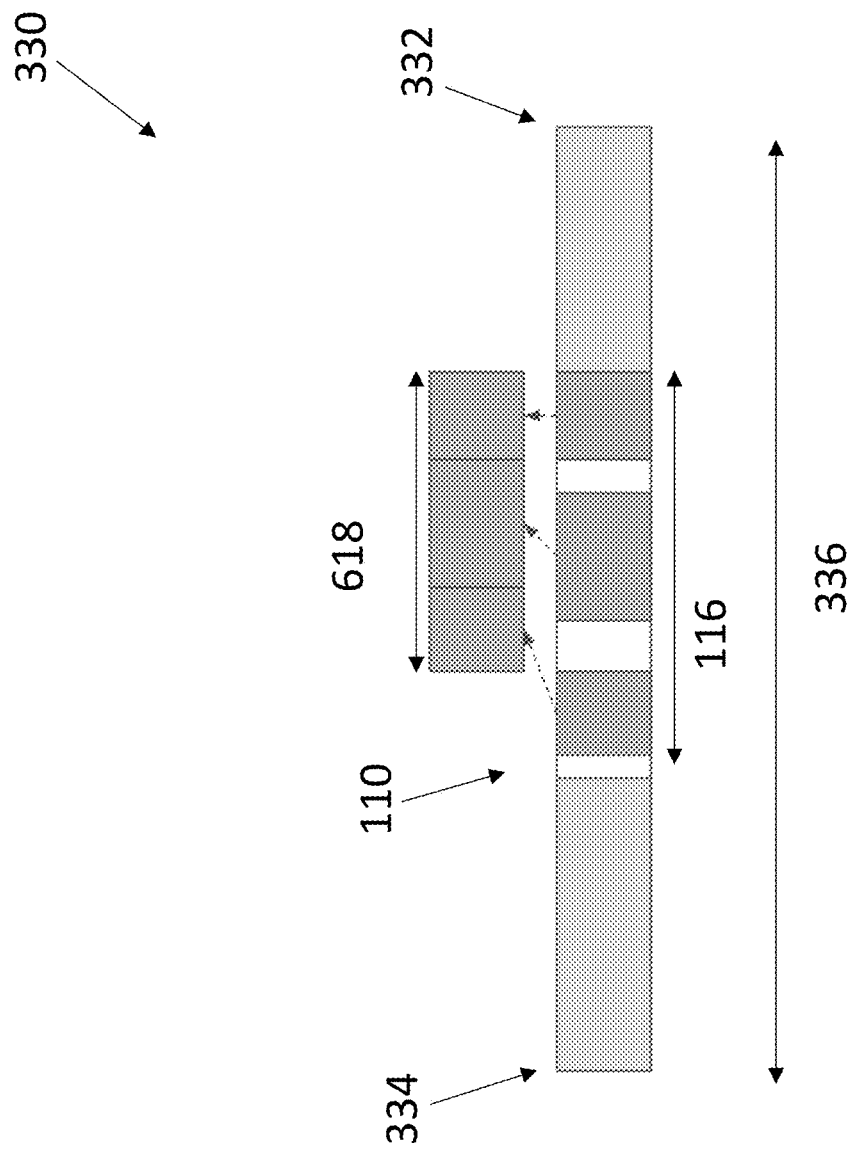
FIG. 6 is a schematic illustration of a process of identifying a set of non-contiguous image frames in an image buffer having quality scores that equal or exceed a quality threshold, and cumulatively stitching the set of non-contiguous image frames to be recorded in a non-volatile memory, in accordance with one or more embodiments of the disclosure.

FIG. 6 depicts the buffer (e.g., cine) memory 330 having the predetermined size 336 and storing one or more sequences of image frames ranging from a time "t-$T_{CINE}$" 332 to a time "t" 334, as described in FIG. 3. The image buffer 110 is shown as constituting a portion of the buffer memory 330, wherein the image buffer 110 has a smaller predetermined size 116 than the predetermined size 336 of the buffer memory 330.

In the example illustrated in FIG. 6, the image frames stored in the image buffer 110 do not have corresponding quality scores equaling or exceeding the first quality threshold as described in FIG. 2. The corresponding quality scores of one or more sets of non-contiguous image frames however may equal or exceed a quality threshold such as the first quality threshold. In this case, the processor 106 may be configured to stitch together non-contiguous image frames that have quality scores equaling or exceeding the first quality threshold and thereby generate a set of cumulative image frames 618 that is automatically recorded in the non-volatile memory 130. By way of non-limiting example, in some embodiments the set of cumulative image frames 618 may be required to have a size (e.g., time length or number of image frames) that is about 70% of the predetermined size 116 of the image buffer 110 before the set of cumulative image frames 618 is automatically recorded in the non-volatile memory 130. Thus, if the processor 106 determines that at least 70% of the image frames in the image buffer 110 have quality scores equaling or exceeding the first quality threshold, even collectively for a set of non-contiguous image frames, the processor 106 may automatically record an ultrasound clip (e.g., comprised of stitched image frames 618) to the non-volatile memory 130. In some cases, each of the sets of non-contiguous image frames that are stitched together must meet a predetermined size criteria before the set of non-contiguous image frames may be included in the set of cumulative image frames 618.

Alternatively or in addition, the processor 106 may provide a smart capture button 140 to enable an alternate ultrasound clip recording, if the non-contiguous image frames have quality scores equaling or exceeding the second quality threshold, but not the first quality threshold. In this fashion, as described in FIG. 3, a user of the ultrasound imaging system 100 may select the smart capture button 140 and enable the system 100 to automatically record an alternate set of cumulative image frames 618.

In some cases, selecting the smart capture button 140 may cause an ultrasound clip of the predetermined size 116 to be recorded in the non-volatile memory 130, possibly without stitching the non-contiguous image frames that equal or exceed the second quality threshold. In some examples, the second quality threshold may be a quality score of 3 on a scale of 1 to 5, or a quality score of 2 on a scale of 1 to 5. The size and quality criteria (i.e., the length and the quality thresholds described herein) may be adjusted as needed or desired.

Figure 7:
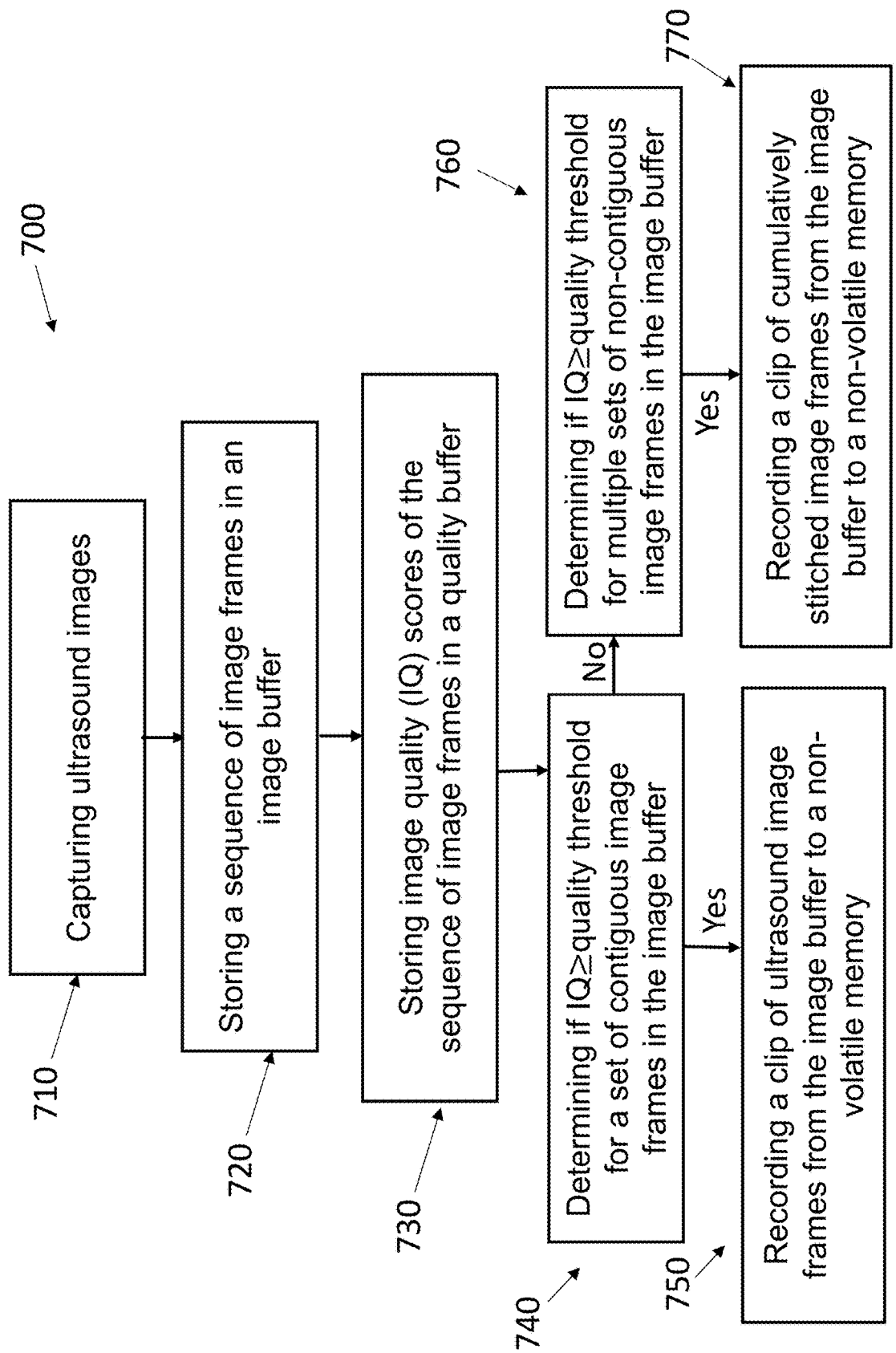
FIG. 7 is a flowchart illustrating a process for activating an automated capture feature or a smart capture feature that can automatically stitch a set of non-contiguous image frames based on quality scores that equal or exceed a quality threshold, in accordance with one or more embodiments of the disclosure.

FIG. 7 is a flowchart 700 illustrating a process that includes recording an ultrasound clip using an automated capture feature based on quality scores of image frames stored in an image buffer, e.g., as described in FIGS. 1-3. At step 710, ultrasound images are captured by a probe such as the ultrasound probe 102 described in FIG. 1. At 720, the ultrasound images are stored in a sequence of image frames in an image buffer such as the image buffer 110 described above.

At 730, a quality score for each of the image frames stored in the image buffer is determined by an image quality detector and stored in a quality buffer (e.g., the quality buffer 120 described in FIG. 1). At 740, a processor of the ultrasound imaging system 100 evaluates the quality scores in the quality buffer and determines whether a set of contiguous image frames in the image buffer have quality scores that equal or exceed a quality threshold, such as the first quality threshold described herein, and whether the set of contiguous image frames is at least a first predetermined size. If the quality scores in the quality buffer indicate that the image buffer contains a set of contiguous image frames of the first predetermined size having quality scores that equal or exceed the first quality threshold, the processor proceeds to step 750 where the processor automatically records an ultrasound clip comprised of at least the set of contiguous ultrasound image frames from the image buffer to the non-volatile memory. On the other hand, if at step 740, after a period of time has elapsed and the processor determines that the image buffer 110 does not contain a set of contiguous image frames of the first predetermined size having quality scores that equal or exceed the first quality threshold, the processor proceeds to step 760 to determine whether the image buffer contains sets of non-contiguous image frames having quality scores that equal or exceed the first quality threshold and if joined together, the sets of non-contiguous image frames could create a cumulative set of non-contiguous image frames having the first predetermined size. In the case of an affirmative determination, the system 100 may automatically stitch (or join) together the sets of non-contiguous image frames meeting the first quality threshold as a cumulative set of non-contiguous image frames and at 770, the system 100 may automatically record a clip comprised of the cumulative set of non-contiguous image frames from the image buffer to the non-volatile memory. While the preceding example illustrates a process that includes determining whether the image frames have quality scores equaling or exceeding the first quality threshold, in other examples the process may include determining whether the image frames have quality scores equaling or exceeding a second quality threshold that may be lower than the first quality threshold.

Figure 8:
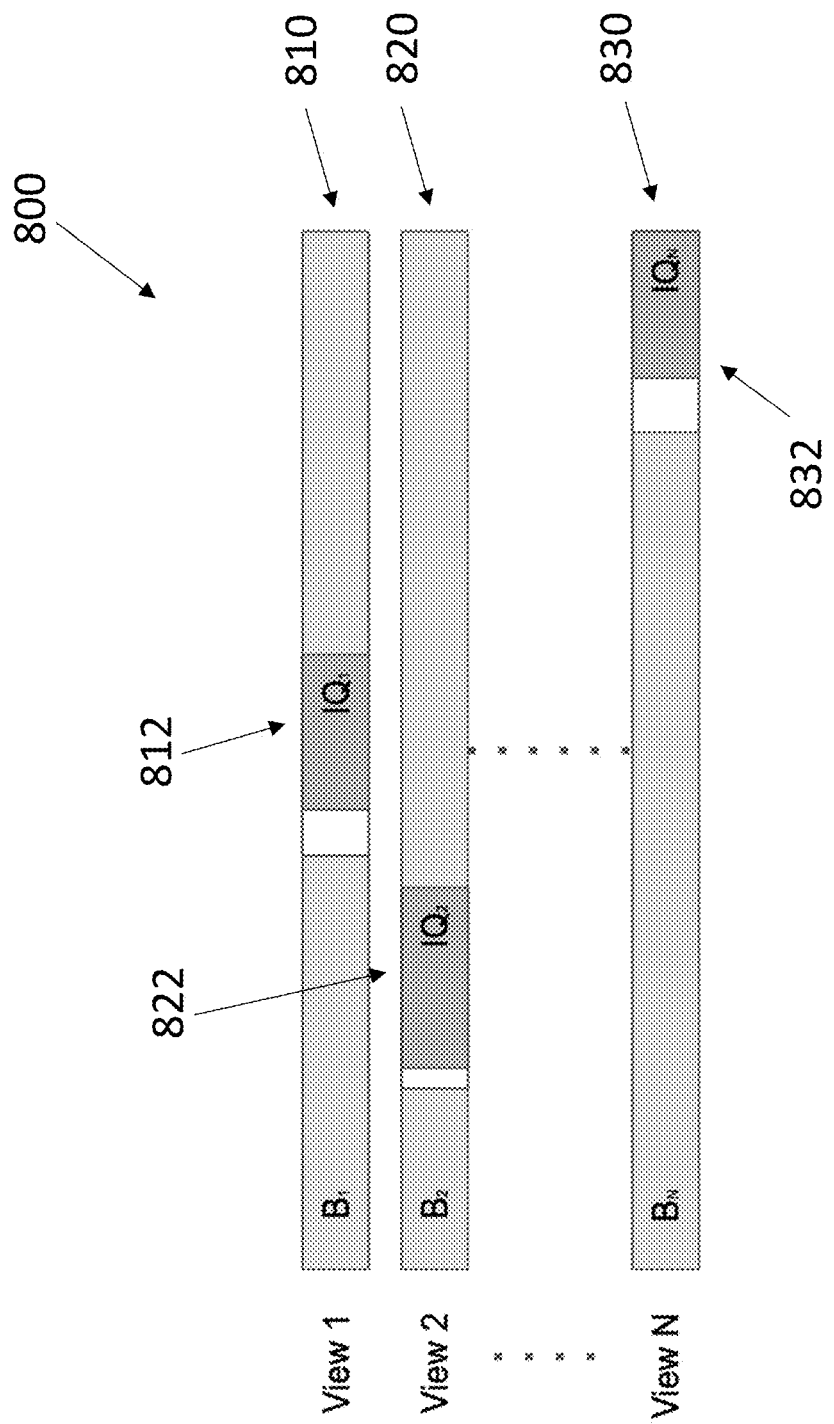
FIG. 8 is a multi-view automated capture arrangement implemented by the automated capture and smart capture features of FIGS. 2 and 3, in accordance with one or more embodiments of the disclosure.

FIG. 8 depicts a multi-view automated capture arrangement 800 in which the ultrasound imaging system 100 implements the automated capture and smart capture features of FIGS. 2 and 3 for a multi-view application. During the course of evaluating a patient, a user of the ultrasound imaging system 100 may scan multiple views of an organ of the patient. As noted earlier, references to "an organ" applies to an organ per se and also to other anatomical structures or body features of the patient. The ultrasound imaging system 100 may be configured to automatically evaluate the ultrasound images captured by the ultrasound probe and detect which view of the organ, such as the heart, is captured in the ultrasound images. For example, the ultrasound imaging system 100 may implement an ultrasound image recognition module as described herein that may be configured to detect known views of the organ (e.g., suprasternal, subcostal, short- and long-axis parasternal, 2-chamber apical, 3-chamber apical, 4-chamber apical and 5-chamber apical views), and output an indication of the detected view. However, not all embodiments of the ultrasound imaging system 100 require implementation of an ultrasound image recognition module.

As with previously-described embodiments, the ultrasound images captured by the ultrasound probe are stored in image frames in an image buffer, such as the image buffer 110. An automated capture feature such as described in FIG. 2 may cause a set of contiguous image frames to be recorded from the image buffer into a non-volatile memory, such as the memory 130.

In some examples, while the user moves the probe relative to the patient to different positions to scan different views of the organ (e.g., the heart), image frames of each view are stored in an image buffer while quality scores for the image frames are stored in one or more quality buffers. The multi-view automated capture feature may detect quality scores for a plurality of sets of contiguous image frames of a first predetermined size that equal or exceed the first quality threshold, each set containing a particular view, and in response, record a plurality of ultrasound clips based on the multiple views to the non-volatile memory 130.

In some embodiments, the multi-view automated capture arrangement 800 includes a plurality of quality buffers, e.g., quality buffers 810, 820, and 830 as shown. The number of quality buffers may vary depending on the number of image quality detectors implemented by the system 100 to assess the quality of the ultrasound images being captured by the ultrasound probe. Each image quality detector may be configured to use a computationally intelligent system that employs artificial intelligence as described earlier herein, to determine a respective quality score for the ultrasound images captured by the ultrasound probe. Each of the image quality detectors may be trained using ultrasound images of known quality for a respective particular view of the organ. In this manner, each image quality detector is tuned to assess the image quality of the ultrasound images according to a respective known view of the organ, assign a quality score to each ultrasound image, and store the quality score in a respective quality buffer corresponding to the particular view that the image quality detector is tuned to evaluate. In some examples, the number of quality buffers may be automatically selected or arranged by the processor 106 based on a recognition of the organ in the ultrasound images and a number of known views of that organ having corresponding image quality detectors in the system 100. In FIG. 8, three quality buffers 810, 820, and 830 are illustrated for simplicity.

The image quality detectors corresponding to the quality buffers 810, 820, 830 may operate simultaneously or sequentially to evaluate the ultrasound images that are captured by the ultrasound probe, with each image quality detector evaluating the ultrasound images according to the respective view of the organ for which the image quality detector was trained. Thus, during or after a sequence of ultrasound images are obtained by the ultrasound probe, the ultrasound images may simultaneously or sequentially be evaluated for image quality by three image quality detectors corresponding respectively to the quality buffers 810, 820, 830. Depending on the particular view in the ultrasound images being captured, two of the three image quality detectors in this example may determine relatively poor quality scores for the ultrasound images because the two image quality detectors are configured to assess the image quality of views that are different than the particular view being captured. On the other hand, the image quality detector that is configured to assess the image quality of the particular view being captured may determine relatively high quality scores for the ultrasound images and record the high quality scores in the respective quality buffer corresponding to the image quality detector.

Embodiments of the ultrasound imaging system 100 that do not specifically implement an ultrasound image recognition module to detect the particular view being captured may use this disparity in quality scores among the different image quality detectors to determine the view that is currently being captured by the ultrasound probe. When, for a particular sequence of ultrasound images, all but one of the quality buffers contain relatively low quality scores and one of the quality buffers contains relatively high quality scores, the ultrasound imaging system 100 may determine which image quality detector corresponds to the one quality buffer having high quality scores and determine that the ultrasound probe is capturing the view for which the determined image quality detector was trained to evaluate.

In some examples, an ultrasound image recognition module may detect the particular view being captured before the image quality detectors determine quality scores for the ultrasound images being captured. In such examples, the processor 106 of the ultrasound imaging system 100 may activate one particular image quality detector corresponding to the detected particular view being captured at the time. This feature may reduce the power and time consumption of the ultrasound imaging system 100 as compared with a system 100 in which all of the image quality detectors are operating. When the user moves the ultrasound probe to a different position relative to the patient and begins capturing ultrasound images of a different view, the ultrasound image recognition module may detect the change of view in the ultrasound images and cause the ultrasound imaging system 100 to deactivate the previous active image quality detector and activate a different image quality detector that was trained to evaluate new view being captured by the ultrasound probe.

An automated capture feature as described in FIG. 2 may be used to identify and record a set of contiguous image frames in the image buffer having a predetermined size and having quality scores that equal or exceed a quality threshold. In some examples, the predetermined size of the set of contiguous image frames and the quality threshold to be met may be the same for each of multiple different views being assessed by the different image quality detectors. Alternatively, for different views being captured, the ultrasound imaging system 100 may require a different predetermined size of the set of contiguous image frames and/or a different quality threshold in order to automatically record an ultrasound clip, based on different requirements for recording an ultrasound clip of a specific view of the organ.

In FIG. 8, the automated capture feature may record an ultrasound clip comprised of a set of contiguous image frames from the image buffer corresponding to a portion 812 of the first quality buffer 810 when the quality scores in the portion 812 equal or exceed the first quality threshold and correspond with a set of contiguous image frames of at least a predetermined size. The ultrasound clip is recorded from the image buffer to a non-volatile memory, preferably in association with the particular view that the image quality detector associated with the first quality buffer 810 is trained to evaluate.

The user of the ultrasound imaging system 100 may move the ultrasound probe 120 relative to the patient to obtain ultrasound images of a second, different view, for example, that corresponds to the view that the image quality detector associated with the second quality buffer 820 is trained to evaluate. While the ultrasound probe is imaging this second view, the quality scores assigned and stored in the second quality buffer 820 may be relatively higher than the quality scores assigned and stored in the first and third quality buffers 810, 830, because the image quality detectors corresponding to the first and third quality buffers 810, 830 are trained to evaluate the image quality of views that are different than the particular view currently being captured. The automated capture feature may record an ultrasound clip comprised of a set of contiguous image frames from the image buffer corresponding to a portion 822 of the second quality buffer 820 when the quality scores in the portion 822 equal or exceed the first quality threshold and correspond with a set of contiguous image frames of at least the predetermined size. The ultrasound clip is recorded from the image buffer to the non-volatile memory, preferably in association with the particular view that the image quality detector associated with the second quality buffer 820 is trained to evaluate.

In a same or similar fashion, the user may again move the ultrasound probe relative to the patient to obtain ultrasound images of yet another different view, for example a third view corresponding to the view that the image quality detector associated with the third quality buffer 830 is trained to evaluate. When the ultrasound probe is imaging this third view, the quality scores assigned and stored in the third quality buffer 830 may be relatively higher than the quality scores assigned and stored in the first and second quality buffers 810, 820, because the image quality detectors corresponding to the first and second quality buffers 810, 820 are configured to evaluate the image quality of views that are different than the particular view currently being captured. The automated capture feature may record an ultrasound clip comprised of a set of contiguous image frames from the image buffer corresponding to a portion 832 of the third quality buffer 830 when the quality scores in the portion 832 equal or exceed the first quality threshold and correspond with a set of contiguous image frames of at least the predetermined size. In various embodiments, the predetermined size of the set of contiguous image frames recorded from the image buffer may be the same as earlier described, for example with respect to the embodiment in FIG. 2. However, in other embodiments, each of predetermined sizes of the set of contiguous image frames for different views may have a different value based on a desired clip length for that particular view.

A smart capture feature may be activated for the multi-view automated capture arrangement 800 when the quality buffers 810, 820, and 830 do not have quality scores that equal or exceed the first quality threshold. If the quality buffers 810, 820, and 830 have quality scores that equal or exceed a second quality threshold and corresponding image frames in the image buffer form a set of image frames of at least a predetermined size, the set of image frames may be recorded in the non-volatile memory as a "best available" clip. In some embodiments, the second quality threshold may be different for each of the quality buffers 810, 820, and 830 based, e.g., on the trained recognition system of the respective image quality detector for the particular view being evaluated by the image quality detector. In some examples, the smart capture feature may cause the system 100 to automatically stitch (or join) together non-contiguous image frames meeting the second quality threshold as an alternative set of non-contiguous image frames and record a clip of the cumulatively stitched image frames, from the image buffer to non-volatile memory, having quality scores that equal or exceed a quality threshold, e.g., as described in FIG. 6.

Figure 9:
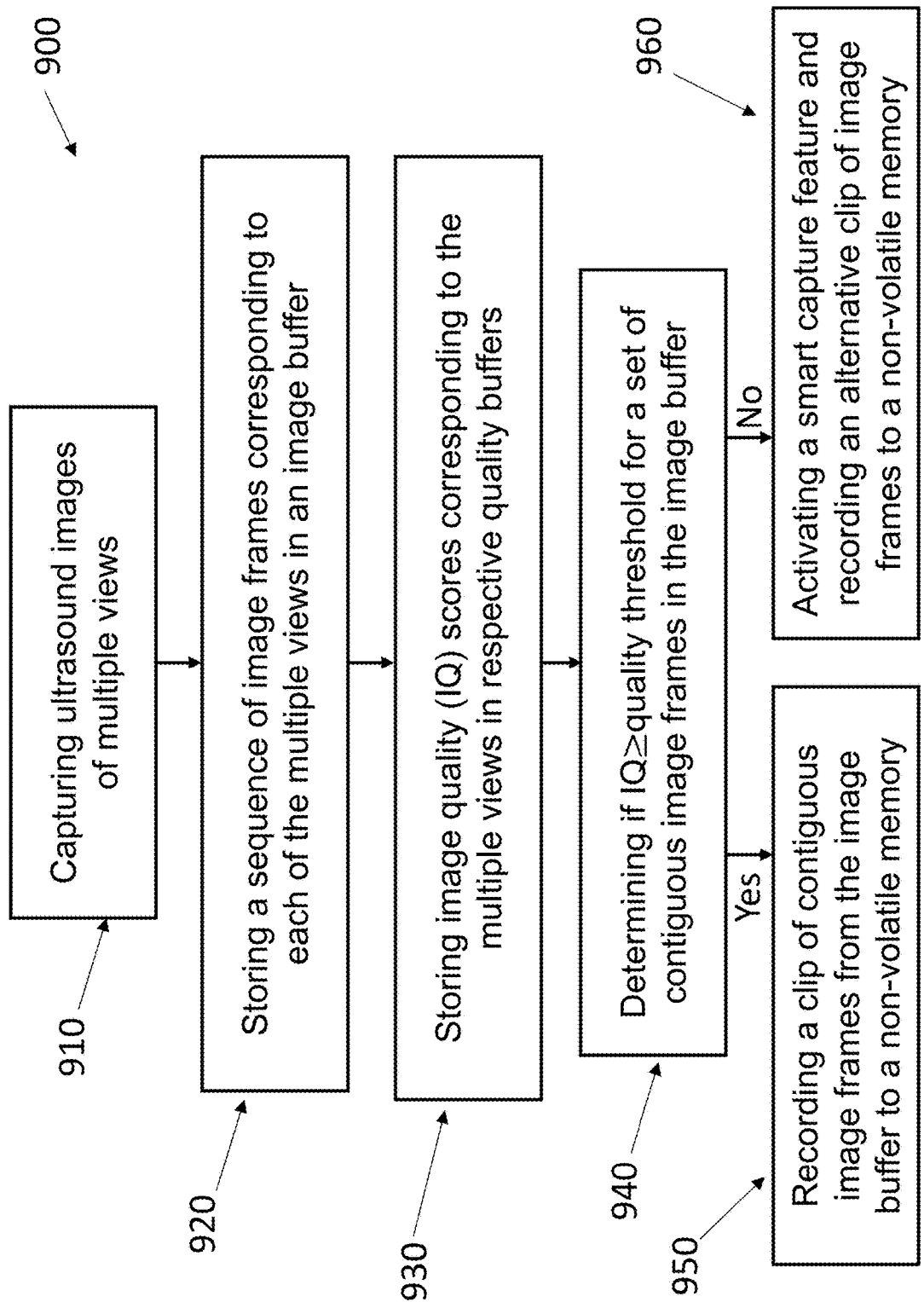
FIG. 9 is a flowchart illustrating a process for automatically recording a multi-view set of image frames based on quality scores of the multiple views that equal or exceed a quality threshold, in accordance with one or more embodiments of the disclosure.

FIG. 9 is a flowchart 900 illustrating a process that includes recording an ultrasound clip using an automated capture feature or, alternatively, a smart capture feature, based on quality scores of image frames stored in the image buffer, e.g., as described in FIG. 8. At 910, ultrasound images are captured by an ultrasound probe such as the ultrasound probe 102 described in FIG. 1. In operation, a user of the ultrasound imaging system 100 may hold the probe 102 against a patient's body at a position and angle to acquire desired ultrasound images of a particular view of an organ, such as the heart. The user may thereafter move the probe to a different position and angle to capture different view of the same organ or even a different organ. In some examples, an automated system as described herein may detect the particular view of the organ being imaged at a given time using a trained image recognition module.

At 920, the ultrasound images for each of the views obtained by the ultrasound probe are stored in one or more sequences of image frames in an image buffer as described in FIG. 8.

At 930, quality scores for each image frame stored in the image buffer are determined by different image quality detectors that are respectively tuned to evaluate particular views. The quality scores determined by the different image quality detectors are stored in different quality buffers (e.g., the quality buffers 810, 820, 830 described in FIG. 8) corresponding to the respective image quality detectors that produced the quality scores.

At 940, a processor of the ultrasound imaging system 100 evaluates the quality scores in each of the quality buffers and determines whether a set of contiguous image frames in the image buffer has quality scores that equal or exceed a quality threshold, such as the first quality threshold described herein, and whether the set of contiguous image frames is at least a predetermined size. If the quality scores in a respective quality buffer indicate that the image buffer contains a set of contiguous image frames of the predetermined size having quality scores that equal or exceed the first quality threshold, the processor proceeds to step 950 where the processor automatically records an ultrasound clip comprised of the set of contiguous ultrasound image frames from the image buffer, corresponding to the particular view meets the quality and size requirements, to the non-volatile memory. On the other hand, if at step 940, after a period of time has elapsed and the processor determines that the image buffer does not contain a set of contiguous image frames of at least the predetermined size having quality scores that equal or exceed the first quality threshold, for any of the views reflected in the quality buffers, the processor proceeds to step 960 and provides a smart capture feature, e.g., a smart capture button 140 as described with respect to FIGS. 1 and 3. A user of the ultrasound imaging system 100 may select the smart capture button which enables the system 100 to automatically record an alternate set of contiguous image frames of a predetermined size having quality scores that equal or exceed a second quality threshold, which may be a lower quality threshold than the first quality threshold. The alternate set of contiguous image frames may constitute an ultrasound clip that includes contiguous image frames from the image buffer having a "best available" quality for one or more particular views. As described in FIG. 3, the alternate set of contiguous image frames may be recorded from the image buffer to the non-volatile memory 130.

It should be appreciated that the various embodiments described above can be combined in different ways to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system for ultrasound imaging, comprising:
an ultrasound imaging device configured to capture ultrasound images, the ultrasound imaging device including:
an image buffer configured to store a sequence of image frames comprised of captured ultrasound images;
a quality buffer configured to store quality scores in a sequence of quality scores that correspond respectively with image frames in the sequence of image frames; and
a computing subsystem configured to:
automatically record, in a memory, an ultrasound clip including a set of contiguous image frames from the image buffer when the corresponding quality score for each image frame in the set of contiguous image frames equals or exceeds a first quality threshold and when the set of contiguous image frames has at least a first predetermined size,
wherein the computing subsystem is further configured to:
provide a smart capture feature when, after a predetermined period of time, the image buffer does not have a set of contiguous image frames of the first predetermined size having corresponding quality scores equaling or exceeding the first quality threshold,
wherein activation of the smart capture feature causes the computing subsystem to automatically record an ultrasound clip including an alternate set of contiguous image frames from the image buffer when the quality score for each image frame in the alternate set of contiguous image frames equals or exceeds a second quality threshold and when the alternate set of contiguous image frames has at least a second predetermined size.

2. The system of claim 1, wherein the first quality threshold is greater than the second quality threshold.

3. The system of claim 1, wherein the first predetermined size for the set of contiguous image frames is different than the second predetermined size for the alternate set of contiguous image frames.

4. The system of claim 1, wherein the smart capture feature includes a user-selectable smart capture button that, when selected by a user, activates the smart capture feature and enables the computing subsystem to automatically record the ultrasound clip including the alternate set of contiguous image frames from the image buffer.

5. The system of claim 1, wherein activation of the smart capture feature causes the computing subsystem to automatically record additional image frames from the image buffer that are contiguous with the alternate set of contiguous image frames but have one or more quality scores that do not equal or exceed the second quality threshold.

6. The system of claim 1, wherein the first predetermined size corresponds to a first predetermined temporal length or number of image frames, and the second predetermined size corresponds to a second predetermined temporal length or number of image frames, and
wherein the second predetermined size is smaller than the first predetermined size.

7. The system of claim 1, wherein the first predetermined size for the set of contiguous image frames corresponds to a first predetermined portion of the image buffer.

8. The system of claim 1, wherein the image buffer is a volatile memory and the memory in which the ultrasound clip is automatically recorded is a non-volatile memory.

9. The system of claim 1, wherein the computing subsystem includes an image quality detector configured to determine the quality score for each image frame according to a particular view that the image quality detector was trained to evaluate.

10. The system of claim 1, wherein the computing subsystem is configured to determine the quality score for each image frame of the sequence of image frames and store a predetermined amount of quality scores in the quality buffer before evaluating the quality scores in the quality buffer to identify the set of contiguous image frames in the image buffer having corresponding quality scores that equal or exceed the first quality threshold.

11. The system of claim 1, wherein the computing subsystem is further configured to:
provide a cumulative recording feature when, after a predetermined period of time, the image buffer does not have a set of contiguous image frames of the first predetermined size having corresponding quality scores equaling or exceeding the first quality threshold,
wherein the cumulative recording feature causes the computing subsystem to automatically stitch multiple sets of non-contiguous image frames from the image buffer when the quality score for each image frame in the multiple sets of non-contiguous image frames equals or exceeds the first quality threshold, and record an ultrasound clip including the stitched sets of non-contiguous image frames from the image buffer.

12. The system of claim 1, wherein the ultrasound imaging device further includes a plurality of quality buffers, each quality buffer of the plurality of quality buffers configured to store quality scores for a sequence of image frames comprised of captured ultrasound images of a respective view of an anatomical structure; and
wherein the ultrasound clip that the computing subsystem is configured to automatically record includes a set of contiguous image frames from the image buffer for the respective view of the anatomical structure when the quality score for each image frame in the set of contiguous image frames equals or exceeds the first quality threshold.

13. The system of claim 12, wherein a different image quality detector is associated with each quality buffer corresponding to a particular view of the anatomical structure.

14. A method for ultrasound imaging, comprising:
capturing ultrasound images by an ultrasound imaging device;
storing, in an image buffer, a sequence of image frames containing the ultrasound images;
determining a quality score for each image frame of the sequence of image frames;
storing, in a quality buffer, the quality score for each image frame of the sequence of image frames, wherein the quality buffer is configured to store the quality score separate from the image frames stored in the image buffer, wherein the quality scores are stored in the quality buffer in a sequence of quality scores that correspond respectively with the image frames in the sequence of image frames;
determining whether each image frame in a set of contiguous image frames in the image buffer has a corresponding quality score that is equal to or greater than a first quality threshold; and
automatically recording, in a memory, an ultrasound clip including the set of contiguous image frames from the image buffer when:
(1) the corresponding quality score for each image frame in the set of contiguous image frames equals or exceeds the first quality threshold, and
(2) the set of contiguous image frames has at least a first predetermined size that is based at least in part on a size of the image buffer, the first predetermined size being defined as a predetermined portion of the image buffer.

15. The method of claim 14, wherein determining the quality score for each image frame includes evaluating the ultrasound image in each image frame using artificial intelligence.

16. The method of claim 14, further comprising:
providing a smart capture feature when, after a predetermined period of time, the image buffer does not have a set of contiguous image frames of the first predetermined size having corresponding quality scores equaling or exceeding the first quality threshold, and
when the smart capture feature is activated, automatically recording an ultrasound clip including an alternate set of contiguous image frames from the image buffer when the quality score for each image frame in the alternate set of contiguous image frames equals or exceeds a second quality threshold and the alternate set of contiguous image frame has at least a second predetermined size.

17. The method of claim 16, wherein providing the smart capture feature includes providing a user-selectable smart capture button that, when selected by a user, enables the ultrasound clip including the alternate set of contiguous image frames to be recorded from the image buffer.

18. The method of claim 16, further comprising displaying an error message when the image buffer does not have an alternate set of contiguous image frames of the second predetermined size having corresponding quality scores equaling or exceeding the second quality threshold.

19. An ultrasound imaging system comprising:
an ultrasound probe coupled to an ultrasound transducer configured to transmit and receive ultrasound signals, wherein the ultrasound imaging system is configured to capture a sequence of image frames, each image frame containing an ultrasound image based on the ultrasound signals;
an image quality detector configured to evaluate each image frame and assign a quality score to each image frame of the sequence of image frames based on a determined quality of the ultrasound image in each image frame;
an image buffer configured to store the sequence of image frames;
a quality buffer configured to store quality scores in a sequence of quality scores that correspond respectively with the image frames in the sequence of image frames; and
a computing subsystem configured to:
determine the quality score for each image frame of the sequence of image frames and store the quality score in the quality buffer, and
automatically record an ultrasound clip including a set of contiguous image frames from the image buffer to a non-volatile memory when the corresponding quality score for each image frame in the set of contiguous image frames equals or exceeds a first quality threshold and the set of contiguous image frames has at least a first predetermined size,
wherein the computing subsystem is further configured to:
provide a cumulative recording feature when, after a predetermined period of time, the image buffer does not have a set of contiguous image frames of the first predetermined size having corresponding quality scores equaling or exceeding the first quality threshold,
wherein the cumulative recording feature causes the computing subsystem to automatically stitch multiple sets of non-contiguous image frames from the image buffer when the quality score for each image frame in the multiple sets of non-contiguous image frames equals or exceeds the first quality threshold, and record an ultrasound clip including the stitched sets of non-contiguous image frames from the image buffer.

20. The ultrasound imaging system of claim 19, wherein the computing subsystem is further configured to provide a smart capture feature when, after a predetermined period of time, the quality score for one or more image frames of a set of contiguous image frames of the first predetermined size is less than the first quality threshold, and wherein activation of the smart capture feature causes the computing subsystem to automatically record an ultrasound clip including an alternate set of contiguous image frames from the image buffer when the quality score for each image frame in the alternate set of contiguous image frames equals or exceeds a second quality threshold and the alternate set of contiguous image frame has at least a second predetermined size.

21. The ultrasound imaging system of claim 20, wherein the smart capture feature includes a user-selectable smart capture button that enables the user to selectively activate the smart capture feature.

22. The ultrasound imaging system of claim 20, wherein the computing subsystem is further configured to display an error message when the quality score of one or more image frames of the alternate set of contiguous image frames is less than the second quality threshold.

\* \* \* \* \*